United States Patent [19]
Gwon et al.

[11] Patent Number: 6,164,282
[45] Date of Patent: Dec. 26, 2000

[54] METHODS FOR RESTORING AND/OR ENHANCING ACCOMMODATION IN PSEUDO PHAKIA

[75] Inventors: Arlene Gwon, Newport Beach; Elizabeth Woldemussie, Laguna-Niguel, both of Calif.

[73] Assignee: Allergan Sales, Inc., Irvine, Calif.

[21] Appl. No.: 09/238,130

[22] Filed: Jan. 27, 1999

[51] Int. Cl.[7] .................................................. A61B 19/00
[52] U.S. Cl. ........................................ 128/898; 623/6.37
[58] Field of Search .................................. 623/6.37, 6.11, 623/6.27, 6.56; 128/898

[56] References Cited

U.S. PATENT DOCUMENTS

| | | |
|---|---|---|
| 4,253,199 | 3/1981 | Banko . |
| 4,254,509 | 3/1981 | Tennant . |
| 4,409,691 | 10/1983 | Levy . |
| 4,790,847 | 12/1988 | Woods . |
| 4,888,012 | 12/1989 | Horn et al. . |
| 4,888,015 | 12/1989 | Domino . |
| 4,932,968 | 6/1990 | Caldwell et al. . |
| 4,976,732 | 12/1990 | Vorosmarthy . |
| 4,994,082 | 2/1991 | Richards et al. . |
| 5,019,098 | 5/1991 | Mercier . |
| 5,171,266 | 12/1992 | Wiley et al. . |
| 5,173,723 | 12/1992 | Volk . |
| 5,275,623 | 1/1994 | Sarfarazi . |
| 5,443,506 | 8/1995 | Garabet . |
| 5,459,133 | 10/1995 | Neufeld . |
| 5,476,514 | 12/1995 | Cumming . |
| 5,488,050 | 1/1996 | Neufeld . |
| 5,496,366 | 3/1996 | Cumming . |
| 5,521,210 | 5/1996 | Woldemussie et al. . |
| 5,562,731 | 10/1996 | Cumming . |
| 5,578,081 | 11/1996 | McDonald . |
| 5,674,282 | 10/1997 | Cumming . |
| 5,716,952 | 2/1998 | Woldemussie et al. . |

OTHER PUBLICATIONS

Thornton, Accommodation in Pseudophakia, 25, pp. 159–162.
Myers Et Al, Journal of Refractive Surgery, V. 14, pp. 136–139, Mar. 1998.
Weber Et Al, Documenta Ophthalmologica, Aug. 1989; 72(3–4): 341–7.
Gabelt Et Al, Exp. Eye Res., 1994, 58, 623–630.
Gilmartin, Ophthal. Physiol. Opt., 1995, 15, 431–437.
Ophthal. Physiol. Opt. vol. 6, No. 1, pp. 23–37, 1986.
Rosenfield Et Al, Ophthal. Physiol. Opt., 1993, vol. 13, 266–284.
Rosenfield Et Al, Ophthal. Physiol. Opt., Jul. 1994, vol. 14, 265–277.
Gilmartin Et Al, Ophthal. Physiol. Opt., Oct. 1991, vol. 11, 304–313.
Gilmartin Et Al, Optometry & Vision Science, vol. 69, No. 4, pp 276–282.
Bullimore Et Al, Documenta Ophthalmologica 69: 385–397, 1988.
Phillips Et Al, Vision Res. vol. 32, No. 9, pp. 1775–1779, 1992.
Optometry and Vision Science, vol. 66, No. 4, pp. 229–234.
Rosenfield Et Al, Current Eye Research, vol. 9, No. 3, 1990, pp. 267–272.
Gilmartin Et Al, Vision Res., vol. 35, No. 9, pp. 1305–1312, 1995.
Bullimore Et Al, Documenta Ophthalmologica 80: 143–155, 1992.
Rosenfield Et Al, Ophthal. Physiol. Opt., vol. 7, No. 4, pp. 359–364, 1987.
Rosenfield Et Al, Ophtal. Physiol. Opt., vol. 7, No. 2, pp. 127–130, 1987.
Strang Et Al, Ophthal. Physiol. Opt., vol. 14, Jul. 1994.
Owens Et Al, Ophthal. Physiol. Opt., vol. 11, Apr. 1991.
Myers Et Al, Journal of Refractive Surgery, vol. 14, Mar. 1998.
Tokoro, Nippon Ganka Gakkai Zasshi (1998), 102(12), 796–812, XP000916765.
Masuda et al., Exp. Eye Res. (1994), 59(6), 729–36, XP000916621.
Poyer et al, Exp. Eye Res. (1994), 59(6), 729–36, XP000916628.
Pang et al, J. Ocul. Pharmacol. (1994), 10(1), 125–36, XP000916627.
Gabelt et al, J. Pharmacol. Exp. Ther. (1992), 263(3), 1133–9, XP000916597.

*Primary Examiner*—Dinh X. Nguyen

[57] ABSTRACT

A method for increasing the amount of accommodation in an eye of a mammal which eye includes an artificial intraocular lens. The method provides for administering to the mammal the amount of a muscarinic agent necessary to restore tonic accommodation.

20 Claims, No Drawings

METHODS FOR RESTORING AND/OR ENHANCING ACCOMMODATION IN PSEUDO PHAKIA

BACKGROUND OF THE INVENTION

The present invention is directed to methods for increasing the ability of the eye to accommodate. More particularly, the invention relates to methods for increasing the amounts of accommodation in mammalian eyes including artificial intraocular lenses (IOLs), more preferably IOLs which are adapted to provide accommodating movement in the eye.

The human eye includes an anterior chamber between the cornea and iris, a posterior chamber, defined by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focusing light rays entering the eye on the retina.

The ciliary muscle controls the shape of the natural lens through suspensory ligaments called zonules. Like most smooth muscles, the ciliary muscle has a dual innervation, receiving both sympathetic and parasympathetic fibers.

The contraction of the ciliary muscle is under parasympathetic or cholinergic control. While this parasympathetic control is predominant, sympathetic, or adrenergic, innervation opposes the cholinergic control and plays a lesser role in enabling relaxation of the ciliary muscle.

After the natural crystalline lens is removed, for example, because of cataract or other condition, a conventional, monofocal IOL can be placed in the posterior chamber. Such IOLs include an optic or lens body adapted to focus light toward the retina of the eye. One or more fixation members or haptics are coupled to the optic and function to fix the IOL in the eye. Such a conventional IOL has very limited, if any, accommodating ability. However, the wearer of such an IOL continues to require the ability to view both near and far (distant) objects. Corrective spectacles may be employed as a useful solution.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference. Such so called accommodating IOLs include an optic or lens body adapted to focus light toward the retina and a movement assembly, having various configurations, coupled to the optic and adapted to cooperate with the eye, for example, with the ciliary muscle of the eye, to move the optic axially to obtain some degree of accommodation. The lenses of the patents noted above in this paragraph are biased to be located in the posterior-most position in the eye under rest or resting conditions. When near focus is desired, the ciliary muscle contracts and the lens moves forwardly (positive accommodation). In the absence of ciliary muscle contraction, the lens moves rearwardly to its posterior-most resting position. One problem that exists with such IOLs is that they often cannot move sufficiently to obtain the desired accommodation.

It would be advantageous to provide methods for increasing the amounts of accommodation in mammalian eyes including IOLs.

SUMMARY OF THE INVENTION

New methods for increasing the amounts of accommodation in mammalian eyes which include IOLs have been discovered. The present methods take advantage of the discovery that muscarinic components, such as muscarinic agonists and muscarinic antagonists, assist or facilitate the action of the ciliary muscle and associated zonules so that the IOL in the eye is effectively moved to provide accommodation, for example, both positive (near) accommodation and negative (far) accommodation. Treatment with a muscarinic component, for example, administering an effective amount of muscarinic component to an eye, preferably is effective to provide increased accommodating movement of the IOL in the eye relative to a substantially identical IOL in a substantially identical eye which is not treated with the muscarinic component. The present methods are convenient to practice and provide outstanding accommodation results, often with substantially no adverse effects to the mammal wearing the IOL.

In one broad aspect of the present invention, methods for increasing the amount of accommodation in an eye of a mammal which includes an artificial IOL comprise administering to the mammal an effective amount of a muscarinic component, such as a muscarinic agonist or a muscarinic antagonist. This administering step preferably is effective to increase tonic contraction of the ciliary muscle of the eye.

The present methods are particularly effective in situations in which the IOL is adapted to move axially in the eye to provide at least some degree of accommodation.

The muscarinic agonist/antagonist preferably is administered in a pharmaceutically acceptable formulation, for example, in a non-irritating sterile solution or suspension. The muscarinic agonist/antagonist more preferably is administered topically to the eye in a pharmaceutically acceptable ophthalmic formulation. In accordance with the present invention, the muscarinic component, that is the muscarinic agonist or muscarinic antagonist, may be selected to act on various muscarinic (M) receptor subtypes of the ciliary muscle.

Any feature described herein or any combination of such features is included within the scope of the present invention provided that the features of any such combination are not mutually inconsistent.

DETAILED DESCRIPTION OF THE INVENTION

With the natural lens in place in the eye, the ciliary muscle acts on the lens to reshape the lens to provide the desired focus accommodation. However, when the natural lens of the eye is surgically replaced by an artificial IOL adapted for accommodating movement, the ciliary muscle often acts to move the optic of the IOL axially in the eye to effect accommodation. Further, the ciliary muscle may be adversely affected by the lens replacement surgery. Also, the size and configuration of the artificial IOL is different from the natural lens. Because of these and other factors, the ciliary muscle benefits from assistance in providing accommodation when the eye includes an artificial IOL. Increasing or enhancing the tone, for example, restoring the natural tone, of the ciliary muscle of an eye including an artificial IOL facilitates or assists the eye in providing accommodation.

In accordance with the present invention, this accommodation facilitation or assistance is provided by the administration of an effective amount of a muscarinic component, as described herein.

The present methods for increasing the amounts of accommodation in the eye of a mammal which eye includes an artificial IOL comprise administering to the mammal an effective amount of a muscarinic component, such as a muscarinic agonist or a muscarinic antagonist. Without wishing to limit the invention to any particular theory of operation, it is believed that the muscarinic component administered as described herein acts to at least assist or facilitate the ciliary muscle, for example, by effecting a parasympathetic response, or blocking or stimulating the parasympathetic system to obtain more effective ciliary muscle tone, in providing accommodation, for example, increased accommodation. This administering step preferably is effective to increase tonic contraction of the ciliary muscle. The administering step very usefully is effective to increase the tone of the ciliary muscle at a neutral resting state of the eye.

As used herein, the term "neutral resting state" refers to the state of the eye which exists without visual stimuli, for example, in a totally darkened room or in a luminous but completely empty visual field. Such a "neutral resting state" can be considered the natural resting state of the eye. The neutral resting state of the eye can be referred to as "tonic accommodation", "space myopia" and "sky myopia". Viewed from a different perspective, the neutral resting state of the eye (with the natural crystalline lens present) exists with the eye focused for objects in a range of about one meter to about two meters from the eye.

In one particularly useful embodiment, the muscarinic components administered in accordance with the present invention, act on one or more muscarinic (M) receptor subtypes of the ciliary muscle.

Muscarinic receptor subtypes enable selective contraction or relaxation of the circular or longitudinal fibers of the ciliary muscle by action on the $M_1$–$M_5$ receptor subtypes.

A summary of receptor subtypes is given in Table 1.

TABLE 1

| Receptor subtype | Tissue or cellular function | Signaling mechanism |
|---|---|---|
| $M_1$ | Contraction or secretion | PI, Ca |
| $M_2$ | Relaxation | cAMP |
| $M_3$ | Contraction or secretion | PI, Ca |
| $M_4$ | Relaxation | cAMP |
| $M_5$ | Contraction or secretion | PI, Ca |

Where:

PI Phosphoinositide hydrolysis (stimulatory response)

Ca Increase in intracellular free calcium (Stimulatory response)

cAMP Decrease in cyclic adenosine monophosphate (AMP) formation (inhibitory response)

The $M_3$ receptor subtype is the most common and is seen predominantly in the circular fibers and the $M_5$ receptor subtype is predominant in the longitudinal fibers. Accordingly, it is possible that the inhibition of the $M_5$ receptor subtype may allow the relaxation/stretching of the longitudinal fibers.

The compounds useful in practicing the present invention include any and all suitable muscarinic agonists or antagonists. As used herein, the term "muscarinic agonists" means any compound that stimulates a parasympathetic receptor subtype to generate a response. Parasympatholytic agents which block the parasympathetic system are muscarinic antagonists and parasympathomimetic agents which stimulate the parasympathetic system are muscarinic agonists. Neuro-effective junctions are considered cholinergic if energized by muscarinic agonists such as acetylcholine.

Without limiting the present invention to specific groups and compounds listed, the following is a list of representative muscarinic agonists and antagonists useful in the present invention:

Muscarinic Agonists

In general, muscarinic agonists are M nonselective and are parasympathomimetic and stimulate the parasympathetic system. Such muscarinic agonists include, but are not limited to:

Pilocarpine

Isopilocarpine lactam

Carbachol

Bethanechol

Methacholine

Muscarine

Muscarinic Antagonists

Muscarinic antagonists are parasympatholytic and block the parasympathetic system.

These antagonists have higher affinity or selectivity for the designated receptor subtype, but they also bind to the other receptor subtypes with a lower affinity. Such muscarinic antagonists include, but are not limited to, in relation to M receptor subtypes:

$M_1$: Pirenzepine, Telenzepine, trihexyphenidyl $M_2$: (+) (11-([2-[(diethylaminomethyl]-1-piperdidinyl}acetyl)-5,11-di-hydro-6H-pyrido(2,3-b)(1,4)benzodiazepine-6-one;

$M_3$: diphenylacetoxy-N-methylpiperidine methiodide, (+) p-fluro-hexahydro-sila-difenidol hydrochloride $M_4$: Pirenzepine, Telenzepine.

Analogs of the foregoing compounds that function as muscarinic agonists are also specifically intended to be embraced by the present invention. The ability of such analogs to function in accordance with the present invention can be tested easily using no more than routine experimentation.

The methods in accordance with the present invention are particularly suited for subjects who are otherwise free of indications for ophthalmic treatments utilizing a muscarinic agonist or antagonist.

The muscarinic components in accordance with the present invention may be administered per se or in the form of pharmaceutically acceptable salts. When used in a formulation, the salts of muscarinic agonists and muscarinic antagonists should be both pharmacologically and pharmaceutically acceptable, but non-pharmaceutically acceptable salts may be conveniently used to prepare the active free compounds or pharmaceutically acceptable salts thereof.

Many of the compounds useful of the present invention are known in the art for other purposes, and are known to be safe under ordinary conditions of use. Thus, the treatment of this invention can be substantially conventionally administered, consistent with known eye treatments, and while avoiding irritation, discomfort or the need for unusual application procedures.

Compositions useful in the present invention may include any suitable formulation from which the presently useful muscarinic components may be delivered to the eye. Preferably, the muscarinic components useful in the present invention are topically administered or applied to the eye. By topical administration, the muscarinic components included in the formulations contact the surface of the eye and penetrate into the deeper tissues of the eye. Such formulations usually include liquid carriers and can be aqueous solutions or suspensions.

Preferably, the muscarinic components in accordance with the present invention are provided in formulations which enhance the duration of activity of the active material on neuro-effective junctions.

The muscarinic components in accordance with the present invention preferably are administered in pharmaceutically acceptable ophthalmic formulations. Such pharmaceutically acceptable ophthalmic formulation produces medically desirable therapeutic effects without concurrently causing clinically significant adverse effects. Clinically significant effects refer to unacceptable side effects of the formulation, including either medically or cosmetically unacceptable effects. Examples of unacceptable side effects include, but are not limited to, reddening or irritated eyes, impaired long distance vision, elevated intraocular pressure, or browache.

With particular reference to pilocarpine, the doses utilized in the present invention fall below that which would cause such side effects.

The muscarinic components in accordance with the present invention are administered in therapeutically effective amounts. A therapeutically effective amount is one which at least assists or facilitates the ciliary muscle in providing accommodation, for example, positive and/or negative accommodation, preferably increased accommodation, in an eye including an artificial IOL. The muscarinic components are typically added to the formulations in accordance with the present invention in amounts in a range of about 0.001% and about 4% by weight of the entire formulation.

The muscarinic components in accordance with the present invention are preferably administered topically and delivered in a medically acceptable, substantially sterile, non-irritating ophthalmic formulation. Ophthalmic formulations may contain pharmaceutically acceptable concentrations of salts, buffering agents, preservatives, viscosity modifiers, osmotic agents and delivery enhancing agents.

Salts which can be used include, but are not limited to, sodium chloride, zinc sulfate, and potassium chloride. Buffers which can be used include, but are not limited to, boric acid and citric acid-based buffers. Preservatives which can be used include, but are not limited to, benzalkonium chloride and edetate disodium. Viscosity modifiers which can be used include, but are not limited to, methyl cellulose, glycerol, and polyethylene glycol. Osmotic agents which can be used include, but are not limited to, sodium chloride, mannitol and sorbitol. Delivery enhancing agents that facilitate the delivery of the therapeutic compound of the invention into the aqueous humor include, but are not limited to, substances which increase corneal permeability, such as surfactants, wetting agents, liposomes, DMSO, and the like. A wetting agent is a substance which facilitates corneal penetration by mildly disrupting the outer corneal surface. A preferred wetting agent is benzalkonium chloride. Other examples of wetting agents include sorbitan esters, polyoxyethylene ethers and the like. These additional materials preferably are present, if at all, in amounts effective to provide the desired benefit or property to the formulation.

It should be understood that although specific formulations have been defined, many variations are possible. The ophthalmic formulations useful in accordance with the present invention preferably are substantially nonirritating and nondamaging to the eye. Normally, such formulations can be applied in a liquid carrier, with an aqueous carrier being preferred although in some instances, quick dissolving forms of the medicaments may be administered in powder form or rubbed into the eye from applicators of various types. Spraying of the eye, the use of eye drops, and other methods of administration or application can be used.

Dosage levels vary greatly depending upon the individual to be treated and the specific medicament used. Proper dosing can be determined without undue experimentation and according to procedures well known to those of ordinary skill in the art.

The formulations preferably are packaged as sterile solutions in dropper bottles, as are well known in the trade. Other containers, including eye cups, can also be used.

The eye to which the muscarinic component is administered includes an artificial IOL, and in particular an artificial IOL adapted to be axially moved in the eye to provide accommodation. Such accommodating IOLs may include, but are not limited to, the IOLs disclosed in Levy U.S. Pat. No. 4,409,691 and Cumming U.S. Pat. Nos. 5,674,282 and 5,496,366. In a very useful embodiment, the accommodating IOL is adapted for bidirectional accommodating movement, that is both anteriorly and posteriorly in the eye, from an intermediate rest position in the eye. Such an IOL is disclosed in commonly assigned U.S. patent application Ser. No. (Attorney Docket No. D-2792), filed Dec. 17, 1998. The disclosure of this application is hereby incorporated in its entirety herein by reference.

In a specific non-limiting example of this invention, a base solution can be formulated as follows (percentages by weight/volume (w/v)): sodium chloride 0.3%; edetate disodium 0.1%; boric acid 1.0%; benzalkonium chloride 0.01%; sodium hydroxide (adjust to pH 6.4) and water. Pilocarpine, at a concentration of 0.1% weight/volume, is added to the base solution.

The above formulation is administered to the eye of a 50-year old human adult which includes a monofocal IOL adapted to move axially in the eye to achieve accommodation. An increased range of axial movement in the eye, evidenced by an increased degree of accommodation, is apparent after administration of the eye drops.

When other muscarinic agonists and various muscarinic antagonists are substituted for pilocarpine, similar results are obtained.

While this invention has been described with respect to various specific examples and embodiments, it is to be understood that the invention is not limited thereto and that it can be variously practiced within the scope of the following claims.

What is claimed is:

1. A method for increasing the amount of accommodation in an eye of a mammal which eye includes a ciliary muscle and an artificial intraocular lens, said method comprising administering to the mammal an effective amount of a muscarinic agonist, the administering being effective to increase tonic contraction of the ciliary muscle.

2. The method of claim 1 wherein the muscarinic agonist is administered topically to the eye in a pharmaceutically acceptable ophthalmic formulation.

3. The method of claim 1 wherein the artificial intraocular lens is adapted to move axially in the eye to provide accommodation.

4. The method of claim 1 wherein the muscarinic agonist is selected from the group consisting of pilocarpine, isopilocarpine lactam, carbachol, bethanechol, methacholine and muscarine.

5. A method for increasing the amount of accommodation in an eye of a mammal which eye includes an artificial intraocular lens, said method comprising administering to the mammal an effective amount of a muscarinic antagonist.

6. The method of claim 5 wherein the eye includes a ciliary muscle and the administering is effective to increase tonic contraction of the ciliary muscle.

7. The method of claim 6 wherein the muscarinic antagonist is administered topically to the eye in a pharmaceutically acceptable ophthalmic formulation.

8. The method of claim 6 wherein the artificial intraocular lens is adapted to move axially in the eye to provide accommodation.

9. The method of claim 6 wherein the muscarinic antagonist is selected to act on $M_1$ receptor subtype of a ciliary muscle of the eye.

10. The method of claim 9 wherein the muscarinic antagonist is selected from the group consisting of pirenzepine, telenzepine and trihexyphenidyl.

11. The method of claim 6 wherein the muscarinic antagonist is selected to act on $M_2$ receptor subtype of a ciliary muscle of the eye.

12. The method of claim 11 wherein the muscarinic antagonist is selected from the group consisting of (+) (11-({2-[diethylaminomethyl]-1-piperdidinyl}acetyl)-5,11-di-hydro-6H-pyrido(2,3-b) (1,4)benzodiazepine-6-one and (+)4,11 dihdro-11-{[(2-[dipropylamino)methyl]-1-piperidinyl) amino]carbonyl}-6H-pyrido (2,3-b) (1,4) benzodiazepine-6-one.

13. The method of claim 6 wherein the muscarinic antagonist is selected to act on $M_3$ receptor subtype of a ciliary muscle of the eye.

14. The method of claim 13 wherein the muscarinic antagonist is selected from he group consisting of diphenylacetoxy-N-methylpiperidine methiodide and (+) p-fluro-hexahydro-sila-difenidol hydrochloride.

15. The method of claim 6 wherein the muscarinic antagonist is selected to act on $M_4$ receptor subtype of a ciliary muscle of the eye.

16. The method of claim 15 wherein the muscarinic antagonist is selected from the group consisting of pirenzepine and telenzepine.

17. A method for increasing the amount of accommodation in an eye of a mammal which eye includes an artificial intraocular lens adapted to move axially in the eye to provide accommodation, said method comprising administering to the mammal an effective amount of a muscarinic agonist.

18. The method of claim 17 wherein the eye includes a ciliary muscle and the administering is effective to increase tonic contraction of the ciliary muscle.

19. The method of claim 18 wherein the muscarinic agonist is administered topically to the eye in a pharmaceutically acceptable ophthalmic formulation.

20. The method of claim 18 wherein the muscarinic agonist is selected from the group consisting of pilocarpine, isopilocarpine lactam, carbachol, bethanechol, methacholine and muscarine.

* * * * *